(12) United States Patent
Matsushita et al.

(10) Patent No.: US 7,270,995 B2
(45) Date of Patent: Sep. 18, 2007

(54) ANALYZING DEVICE

(75) Inventors: Hirohisa Matsushita, Saitama-ken (JP);
Hidenori Kawai, Saitama-ken (JP);
Takashi Kitoh, Saitama-ken (JP)

(73) Assignee: Nichirei Biosciences, Tokyo (JP)

( * ) Notice: Subject to any disclaimer, the term of this patent is extended or adjusted under 35 U.S.C. 154(b) by 0 days.

(21) Appl. No.: 10/296,383

(22) PCT Filed: Dec. 19, 2000

(86) PCT No.: PCT/JP00/08991

§ 371 (c)(1),
(2), (4) Date: Nov. 25, 2002

(87) PCT Pub. No.: WO01/90753

PCT Pub. Date: Nov. 29, 2001

(65) Prior Publication Data
US 2003/0143639 A1    Jul. 31, 2003

(51) Int. Cl.
*C12M 1/36* (2006.01)
*C12M 1/38* (2006.01)
*C12M 3/00* (2006.01)

(52) U.S. Cl. .................. 435/287.2; 436/514; 436/518; 436/164; 436/165; 436/169; 436/528; 436/530; 436/805; 436/807; 436/808; 436/810; 436/811; 435/7.1; 435/7.2; 435/7.93; 435/7.94; 435/970; 435/974; 435/975

(58) Field of Classification Search ................ 436/514, 436/518, 164, 165, 169, 528, 530, 805, 807, 436/808, 810, 811, 817; 435/7.1, 7.2, 7.93, 435/810, 7.94, 970, 7.95, 974, 7.92, 975, 435/287.7, 287.2, 287.6
See application file for complete search history.

(56) References Cited

U.S. PATENT DOCUMENTS

| | | | | |
|---|---|---|---|---|
| 4,857,453 A | * | 8/1989 | Ullman et al. | 435/7.92 |
| 4,861,711 A | * | 8/1989 | Friesen et al. | 435/7.92 |
| 4,960,691 A | * | 10/1990 | Gordon et al. | 435/6 |
| 5,356,782 A | * | 10/1994 | Moorman et al. | 435/7.9 |
| 5,468,648 A | * | 11/1995 | Chandler | 436/518 |
| 5,559,041 A | * | 9/1996 | Kang et al. | 436/518 |
| 5,726,010 A | | 3/1998 | Clark | |
| 5,728,587 A | * | 3/1998 | Kang et al. | 436/518 |
| 5,939,252 A | * | 8/1999 | Lennon et al. | 435/4 |
| 6,194,225 B1 | * | 2/2001 | Oka et al. | 436/518 |
| 6,528,323 B1 | * | 3/2003 | Thayer et al. | 436/518 |
| 6,582,970 B1 | | 6/2003 | Manita | |

FOREIGN PATENT DOCUMENTS

| | | |
|---|---|---|
| CN | 1124524 A | 6/1996 |
| EP | 0 286 371 A2 * | 12/1988 |
| EP | 0 322 340 A2 | 6/1989 |
| EP | 291194 | 10/1989 |
| JP | 1-503174 | 10/1989 |
| JP | 7-55808 | 3/1995 |
| WO | WO90/09592 A1 | 8/1990 |
| WO | WO92/21977 A1 | 12/1992 |
| WO | WO94/23300 A1 | 10/1994 |
| WO | WO 00/77524 A1 | 12/2000 |

* cited by examiner

*Primary Examiner*—Bao-Thuy L. Nguyen
(74) *Attorney, Agent, or Firm*—Sughrue Mion, PLLC (57) ABSTRACT

The present invention is an analytical device which comprises a porous piece assembly consisting of a liquid reagent-receiving porous piece (1), a labeled substance-retaining piece (2), a test piece (3) comprising a detection site (4) and a reference site (5), and a sample-absorbing porous material piece (6); and a sample-receiving porous material piece (7) disposed independently therefrom and partially communicated therewith through a connection. The analytical device of the present invention exhibits extremely high sensitivity and can accurately perform various types of analysis.

19 Claims, 1 Drawing Sheet

Fig. 1 downstream ← liquid flow → upstream

ANALYZING DEVICE

This application is a National Stage entry of PCT/JP00/08991.

BACKGROUND OF THE INVENTION

The present invention relates to an assay using specific binding, for example, an immunoassay, also referred to as immunochromatography.

Currently, there are analytical devices based on the principle of immunochromatography for simple diagnoses of infectious diseases. These analytical devices have better operability and enable measurement in a shorter time, compared to a variety of other conventional testing devices and kits. However, completely satisfactory sensitivity is not yet achieved, and measurement is not possible for some items.

The methods utilizing an immunoassay that have been proposed comprise the steps of applying a sample onto a part of a test piece; allowing the sample to penetrate and infiltrate the test piece using a liquid to reach a detection area of the piece; fixing an analyte contained in the sample to a specific binding reagent immobilized on the detection area of the test piece while the sample is passing through the detection area; and determining the fixed analyte using a labeled reagent. Specific examples of the prior art using this principle are described in GB1589234 of TYROID DIAGNOSTICS INC., and EP022505 of BOOTS-CELLTECH DIAGNOSTICS LIMITED.

An improved technique has been proposed that is based on the above technique and comprises the steps of providing a porous member having a specific substance immobilized on a detection zone and a labeled reagent within a hollow casing made of a moisture-impermeable material; allowing a liquid sample to reach the detection zone while first reacting with the labeled reagent, and to form a complex with the immobilized specific substance; and determining the degree of the binding (Japanese Patent Examined Publication (kokoku) No. 7-46107: Unilever N.V. (NL)).

This proposal is clearly superior to the prior art in that the proposed method can provide a more rapid and convenient analysis, and in particular, it is appropriate for domestic use. This is achieved by placing a test piece within a hollow casing wherein an analyte and a labeled reagent, while reacting with each other, migrate in a porous material by capillary action to reach a detection zone, whereby reacting with the specific binding substance immobilized on the detection zone. However, further improvement is expected because all the reactions are performed simultaneously in a one-step process, so that the labeled reagent is easily affected by an excess amount of reactants and reaction-interfering substances.

SUMMARY OF THE INVENTION

The present invention has been achieved in the light of the above-described current state of the art. Therefore, an object of the present invention is to provide an analytical device which is capable of conveniently measuring analytes with an improved sensitivity while controlling the effect of reaction-interfering substances contained in a sample.

According to the present invention, there is provided an analytical device comprising a test piece in a hollow casing made of a moisture-impervious material, said test piece being made of a dry porous material in which a sample is freely mobile in the wet state, wherein a specific binding substance is immobilized at a detection site on the dry porous material stably even when in the wet state, and another specific binding substance labeled directly with a signal-generating substance is retained at a site physically distant from said detection site in such a manner that the labeled specific binding substance is mobile in the wet state, whereby a sample first contacts with said specific binding substance immobilized on said porous material to form a first complex between an analyte in the sample and said specific binding substance, and said directly labeled specific binding substance is then wetted and reaches said detection site to bind to said first complex, said device being adapted in such a manner that the extent of the binding can be observed, and wherein said device is adapted in such a manner that a liquid sample first contacts with said specific binding substance stably immobilized at said detection site on said porous material, indirectly through a sample-receiving dry porous member.

DESCRIPTION OF THE INVENTION

The present invention has been made in order to achieve the above object. After devoting considerable efforts to research and investigation from all aspects, the present inventors drastically transformed the above ideas. Specifically, the present invention does not employ the standard method which involves directly mixing a sample with a labeled reagent for reaction to proceed at a detection site, in other words, performing all the reactions simultaneously in a single step. Instead, the present invention employs a method which involves adding a sample totally independently to a reaction system, so as to allow an analyte to react at the detection site, and after the reaction, allowing the analyte to react with a labeled reagent; in other words, the analyte does not react with the labeled reagent from the beginning, but reacts with the reagent afterwards, as it were, indirectly. Thus, the present inventors have obtained a useful new finding that an analyte can be measured by this method conveniently with an increased sensitivity while controlling the effect of the reaction-interfering substances contained in the sample, and thus resulted in a novel analytical device based on the two-step reaction.

According to the present invention, there is provided an analytical device, which employs the two-step reaction, wherein an analyte in a sample first reacts with a specific binding substance immobilized on a detection site, a first portion of a labeled reagent reaches the detection site by capillary action within a porous material and passes through the detection site while washing off an excess amount of reactants and reaction-interfering substances, and then the remaining labeled reagent reacts effectively with the immobilized analyte, thereby improving the sensitivity. Further, the analytical device comprises a test piece in a casing made of a moisture-impermeable material in which the above components are disposed so as to enable efficient and convenient detection and analysis of an analyte.

The present invention is hereafter described in detail.

An exemplary case where reaction-interfering substances may be contained in a liquid is, for example, the detection of an IgG antibody against a virus in human serum. A virus antigen may be used as a specific binding substance immobilized on a detection site, and an anti-human IgG antibody may be used as a labeled reagent. However, only very weak binding is observed in the one-step reaction for the following reasons. Since the amount of IgG antibody against the virus is very low compared to the total amount of IgG contained in human serum, most of the labeled reagent will react with human-derived IgG contained in the sample, instead of reacting with the IgG antibody against the virus, when the labeled reagent and serum are brought into contact with each other. In the method of the present invention, in contrast, the virus antigen as a specific binding substance immobilized on the detection site can first react efficiently with the IgG antibody against the virus in a sample, without cross-reacting with other IgG contained, for example, in serum, then the labeled anti-human IgG antibody reagent can reach the detection site and the detection site can be washed by an initial small amount of the reagent solution, and thereafter the directly-labeled anti-human IgG antibody can bind to the human anti-virus IgG antibody immobilized on the detection site. Thus, the present invention enables efficient detection and analysis while minimizing the effect of reaction-interfering substances.

Moreover, the one-step reaction is known to be low in reactivity when an excess amount of analyte is present in a sample. This occurs when an excess amount of analyte reacts with a large amount of an immobilized specific binding substance and with a large amount of a labeled reagent. This is also known as the "hook effect", in which no complex can be formed from the immobilized specific binding substance, analyte and labeled substance, resulting in a low apparent reaction. Due to the hook effect, there may be a case that an analyte cannot be detected when a sample containing an excess amount of analyte is measured according to the principle of one-step reaction. In the present invention based on the principle of two-step reaction, however, after an analyte in a sample first reacts with all the immobilized specific binding substance, a labeled reagent reaches the detection site and an excess amount of the analyte existing in the detection site is washed off with an initial small amount of a reagent solution and then the labeled reagent can efficiently bind to the analyte fixed to the detection site, so as to form a complex therewith, thereby enabling observation of the resulting complexes.

In an embodiment of the present invention, a polyclonal antibody having polyvalent reactivities can be used as a labeled substance and/or an immobilized specific binding substance to increase sensitivity. In the standard method based on the principle of one-step reaction, a labeled reagent comprising a polyclonal antibody having specificities to many different epitopes of an analyte, first reacts with the analyte. Accordingly, when the labeled reagent and analyte reach the detection site, most of the specific epitopes of the analyte are bound to and coated by the labeled reagent, and there is almost no binding of the labeled substance to the detection site. Therefore, the standard method should often employ a substance having specificity to one epitope of an analyte, such as a monoclonal antibody, as the labeled substance. Further, the detection site must have specificity to an epitope which is different from the epitope that the labeled substance recognizes. When a polyclonal antibody that has specificities to many different epitopes of an analyte is used as a labeled reagent in the present invention, an unlabeled substance immobilized on the detection site and specific to the analyte completely reacts with the analyte in the first reaction; and then the labeled reagent reacts with the immobilized analyte in the second reaction, so that the labeled reagent is efficiently bound to the detection site. If the analyte has 3 or more epitopes, the analyte which has been bound to the detection site in the first reaction, can be bound to the labeled reagent at a rate of 1:2 or more in the second reaction. In this case, sensitivity can be easily enhanced.

One important feature of the present invention is, rather than employing a conventional homogeneous (one-step reaction) measurement system involving a simultaneous reaction of an immobilized, unlabeled specific substance, an analyte and a labeled reagent, but to enable convenient measurement by a heterogeneous (two-step reaction) measurement system in which an unlabeled specific substance immobilized on the detection site and an analyte form a complex in the first reaction, and the complex then reacts with a labeled reagent in the second reaction, resulting in an enhanced sensitivity while minimizing the effect of the reaction-interfering substances contained in a sample.

A typical embodiment of the analytical device of the present invention comprises a dry porous carrier, which is disposed such that an analyte in a sample first reacts with an unlabeled specific binding substance which has been immobilized stably even in wet condition at a detection site on the porous material, and a labeled reagent which specifically binds to the analyte and is mobile in wet condition is disposed at a site different from the detection site such that it can infiltrate to the detection site when a liquid other than the sample is added. The device also comprises a casing formed of a moisture-impermeable solid material for accommodating an analytical test piece so that the degree of binding of the labeled reagent to the detection site can be observed. In the analytical device, the test piece-accommodating casing is directly or indirectly communicated with the detection site on the porous carrier so as to be capable of supplying a liquid sample to the detection site. The analytical device is configured such that, after the analyte in the sample first binds to the specific binding substance immobilized stably even in wet condition at the detection site, the analytical test piece-accommodating casing can supply a liquid solution directly or indirectly to the labeled reagent. The labeled reagent thus wetted with the solution reaches the detection site, and then binds to the immobilized analyte while washing off the excess sample. The analytical device also comprises a means for observing the degree of such binding.

Another embodiment of the device according to the present invention which is used for assay or analysis of analytes comprises at a detection site an immobilized specific binding substance which is unable to migrate in wet condition. The design of the device allows an analyte in a sample to first bind to the specific binding substance, so as to be immobilized on the porous material. The device also comprises in a region different from the detection site a porous solid member which retains a reagent comprising a labeled substance specifically binding to the analyte. The labeled reagent is retained at the position while the porous member is in dry condition, but becomes capable of being freely mobile in the porous member when wetted by a liquid reagent. Accordingly, the labeled reagent migrates to the detection site located apart from the site at which the labeled reagent is retained. Thus, the labeled reagent migrates while removing an excess amount of the sample and analyte existing at the detection site, and reacts with a complex of the analyte in the sample and the specific binding substance immobilized on the porous material. Finally, the analyte in the sample is sandwiched between the immobilized specific binding substance and the labeled reagent. The device comprises a test piece-accommodating casing formed from a moisture-impermeable solid material through which the binding at the detection site can be observed.

A further embodiment of the device according to the present invention which is used for assay or analysis of analytes comprises a specific binding substance which is immobilized at a detection site and does not migrate in wet condition. The design of the device allows an analyte in a sample to first and indirectly or directly bind to the specific binding substance, so as to be immobilized on a porous material. The device also comprises in a region different from the detection site another porous solid member which retains a labeled reagent comprising an analyte or its analog. The labeled reagent is retained at the position while the porous member is in dry condition, but becomes capable of freely moving in the porous member when wetted by, for example, a liquid reagent. Accordingly, the labeled reagent migrates to the detection site which is located at a position apart from the site at which the labeled reagent has been retained. The labeled reagent migrates while removing an excess amount of the analyte and sample existing at the detection site, and competitively reacts with a complex of the analyte in the sample and the specific binding substance immobilized on the porous material. Eventually, the immobilized specific binding substance and analyte inhibit reaction between the labeled reagent and the specific binding substance. The device comprises a test piece-accommodating casing formed from a moisture-impermeable solid material through which this binding condition at the detection site can be observed.

As a method for applying a sample to the device, an indirect method which involves applying a sample through a porous member is used in the present invention. For example, a sample is applied to a sample-applying hole of the device and then transferred to a detection site via a certain member, such as a sample-receiving porous piece of a different material from the porous material having the detection site, which has such a structure that the member and the detection site are at least partially in contact with each other so as to allow efficient migration of the sample to the detection site. Hence, a user can easily apply a sample indirectly to the detection site. In an important preferred embodiment of the present invention, it is necessary that the components be disposed such that a sample is indirectly applied to the detection site and can react first with an unlabeled specific binding substance which is stably immobilized even in wet condition at the detection site on the porous material. For example, a sample-receiving porous member of a different material from the porous material on which the detection site is located may be used; this member is in contact with the detection site so as to allow efficient migration of the sample to the detection site. The sample-receiving porous member may have any appropriate size and shape, such as square, rectangle, triangle to polygon, circle, oval, or rhomboid. When the sample-receiving porous member is a separate member from the porous material having the detection site, the porous member is disposed such that at least one end of the member overlaps with the porous material, or the porous member and the porous material may be connected using a material which allows migration of sample, for example, filter paper or glass wool. In that case, the member and the material may be connected using one or more strips of filter paper or the like, or they may be connected using a pipe charged with such a material. If desired, the member and the material bound or connected to each other may be punched or formed together.

Any material may be used as the porous member or piece, so far as it has wettability. Generally, glass wool, cellulose, nitrocellulose and the like can be used as the sample-receiving porous member. When the member has low hydrophilicity, pretreatment using a surfactant or the like may be performed to allow smooth migration of a sample to the detection site. An important requirement for the sample-receiving porous member used herein is to allow smooth and rapid migration of a sample to the detection site. Therefore, it is preferred that the porous member does not interact with an analyte contained in a sample, and has low adsorption to an analyte. Furthermore, the use of a material having low water holding capacity is preferred, so that even when more than a necessary amount of a sample migrates and flows into the detection site, the flow of a directly labeled substance is not obstructed in the second reaction. Glass wool can be used as a preferred example to satisfy such a requirement.

By supplying the sample through the porous member to the detection site as described above, insoluble substances which may be contained in the sample can be removed. In addition, a plurality of materials may be used together in the sample-receiving porous member.

In one embodiment of the present invention, a wall or barrier for inhibiting inflow of a sample may be disposed between the detection site and a region for retaining a directly labeled substance. When a sample is applied to the detection site in the first operation, the sample spreads radially from the applied site. If the applied sample is present in a large amount, the sample may reach the region for retaining the labeled substance before the second reaction proceeds. This can be prevented by disposing the barrier for inhibiting the inflow of a sample, which is provided by applying aqueous sucrose, aqueous glycerol or the like followed by drying, between the detection site and the region for retaining the labeled substance. When the sample reaches the barrier, the flow of the sample stops at the inhibition barrier, thereby preventing contact of the sample with the directly labeled substance before the start of the second reaction. After the second operation is performed, the barrier is dissolved by the sample or a liquid reagent for the second reaction, and then the labeled substance reaches the detection site to perform reaction. Another advantage is that mixing of a sample and a directly labeled substance is minimized by the barrier for inhibiting the inflow of a sample.

An embodiment of the present invention is a device comprising a casing for accommodating an analytical test piece, which is formed from an impermeable solid material and provided with an opening or hole for applying a liquid reagent to perform the second reaction. Preferably, a detection site, a directly labeled reagent and a hole for applying a liquid reagent are physically disposed in this order, thereby enabling wetting of a dry labeled reagent existing in a region physically different from the detection site to allow free migration in the direction toward the detection site within the porous carrier. The detection site, the region of the directly labeled reagent, and the application hole are all linked together with porous material members, so that a liquid can migrate by capillarity action. It is desirable to employ filter paper as a porous material for the second reaction between the directly labeled reagent and the application hole. It is also required for the porous material for the second reaction to wet a directly labeled reagent to allow the reagent to reach the detection site, and then to migrate beyond the site. Thus, a preferred porous material herein for the second reaction can constantly provide the porous material having the detection site with a fixed amount of a liquid, so that the directly labeled reagent can flow at a constant rate on the porous material toward the detection site. For this system to function stably, filter paper or the like is the best example of such porous material, because it retains a fixed amount of a liquid which is sufficient for migration of the directly labeled reagent. The preferred device is designed so that after a sample is applied into the sample-applying hole disposed near the detection site, a reagent solution is then applied from a pipette, a dropping bottle or the like to the inlet for the reagent to start the second reaction, and a few minutes later, preferably about 3 to 10 minutes later, an analysis result can be obtained.

A preferred embodiment of the present invention is a device wherein a liquid reagent to be supplied for performing the second reaction is provided in a test piece-accommodating casing formed from a moisture-impermeable solid material. In this device, it is preferred that a detection site, a directly labeled reagent and a tank for containing the liquid reagent are physically disposed in this order, thereby enabling wetting of the dry directly labeled reagent existing in a region physically different from the detection site to allow free migration of the reagent within the porous carrier, in the direction toward the detection site. The detection site, the directly labeled reagent, and the tank are all linked together with porous material members, so that the liquid can migrate by capillarity action. It is desirable to employ filter paper as a porous material for the second reaction between the directly labeled reagent and the tank. It is also required for the porous material for the second reaction to wet a directly labeled reagent, allowing the labeled reagent to reach the detection site, and then to allow the labeled reagent to migrate beyond the region. Thus, a preferred porous material for the second reaction can constantly provide the porous material having the detection site with a fixed amount of a liquid, so that the directly labeled reagent can flow at a constant rate on the porous material toward the detection site. For this system to function stably, filter paper or the like is the most appropriate example of such materials, because it retains a fixed amount of a liquid which is sufficient for migration of the directly labeled reagent. For example, a tank for storing a liquid reagent is previously provided in a plastic casing. The device is designed so that after a necessary amount of a liquid reagent is stored in the tank, the tank is normally sealed with, for example, an aluminum sheet by heating to prevent contact of the liquid with the porous material. To start the second reaction, this aluminum seal is broken with a sharp pin or the like to wet the porous material for the second reaction, allowing the reaction to proceed. Another possible method to perform the second reaction involves sealing a liquid reagent within an aluminum bag which is retained by the test piece-accommodating casing.

It is important in all the embodiments of the present invention that after a sample is applied in the first operation, all the solutions provided in the second operation flow toward the detection site from the position at which the directly labeled reagent is located, whereby the reagent migrates to and passes through the detecting site. Moreover, it is preferable that the reagent is allowed to continue to flow even after the reagent has passed through the detection site, which enables the labeled substance not involved in the reaction to be washed away, thereby enabling provision of clearer signals. For this purpose, an absorbing porous material can be provided to absorb a solution that has passed through and flows from the detection site. Filter paper or the like can be used as the absorbing porous material.

In an embodiment of the present invention, a reference area may be included. When a reference area is included, the area can be designed to show that the device is functioning satisfactorily. For example, when a directly labeled reagent comprises a mouse antibody, an anti-mouse antibody may be immobilized in the reference area, so that satisfactory operation of the device can be confirmed.

In a preferred embodiment of the present invention, nitrocellulose is selected as the porous carrier, because of its inherently high ability of binding to protein without the need of previously increasing its sensitivity. In addition, nitrocellulose of various pore sizes (porosities) is available, so that appropriate nitrocellulose can be selected depending on the particle size of directly labeled substances. As a label used in the directly labeled reagent according to the present invention, known substances, such as gold colloid, dye sol and latex, can be used. With these substances, analytical results of complexes accumulated in the testing site can be obtained instantly without requiring any special device.

In a preferred important embodiment of the present invention, colored latex particles and gold colloid can be used as labels in the labeled reagents. These substances are characterized in that direct detection is possible using the direct label's own color as a signal.

In a preferred important embodiment of the present invention, nitrocellulose can be used as a porous material. This material is capable of adsorbing protein, such as an antibody having binding specificity, by physical adsorption, so that protein can be easily immobilized stably in wet condition. Specifically, after the protein is immobilized onto nitrocellulose, inactive substances in reaction, such as bovine serum albumin, may be used to block unnecessary sites, so as to prevent protein to be analyzed from adsorbing to such sites.

Some preferred embodiments of the present invention will be hereinafter described in detail with reference to the attached drawings. However, the following explanation is given for illustrative purposes only.

Figure 1:
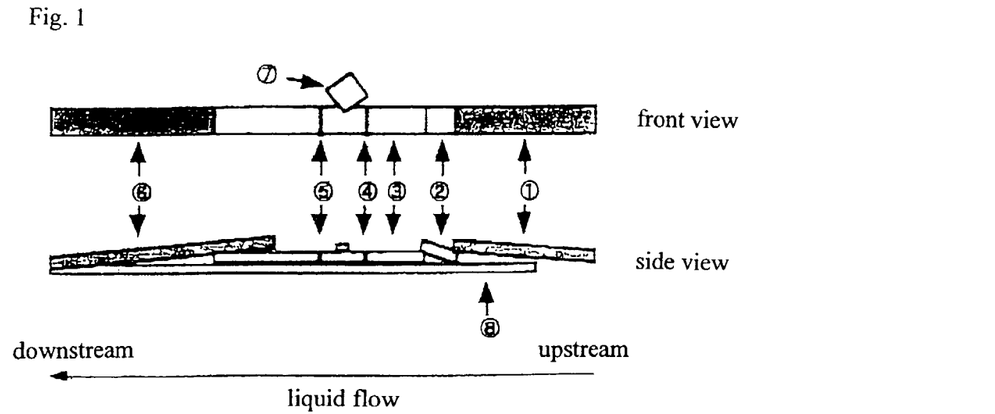
FIG. 1 shows a basic configuration of an analytical device according to the present invention.

FIG. 1 shows a typical test piece made of a porous material to be used in the assay of the present invention, illustrating the operation principles thereof. The front view in FIG. 1 shows schematically the surface from which an analyst observes assay results, and the side view shows a schematic diagram of the test piece seen laterally. For convenience of explanation, the flow direction of a labeled reagent is shown with an arrow from the right to the left side, and the downstream side is shown on the left and the upstream side is shown on the right. All the porous materials, pieces or members are fixed onto a porous support 8, and are linked so as to allow migration of an applied liquid sample and reagent by capillarity action.

A test piece 3 includes a detection site 4, onto which a specific binding substance is immobilized in the form of a line such that it is not detached even in wet condition. The test piece 3 also includes a reference site 5, to which a substance specifically binding to the labeled substance is immobilized in the form of a line such that it is not detached even in wet condition. The detection site 4 is disposed upstream of the reference site 5 and downstream of a site 2 for retaining the labeled substance. The detection site 4 and the reference site 5 may be disposed at any positions, so far as the two positions are distinguishable from each other. A porous piece or member for retaining the dry labeled substance at the site 2 is disposed upstream of the detection site 4, such that when wetted the labeled substance is dissolved and transferred to the test piece 3. An absorbing porous piece or member 6 is disposed downstream of the reference site 5 on the test piece 3. The porous piece 6 absorbs a liquid sample and reagent flowing from the test piece 3 by capillarity action. A liquid reagent-receiving porous piece or member 1 is disposed upstream of the porous piece for retaining the dry labeled substance at the site 2, such that it is communicated with the porous piece 2. In the second operation, the liquid reagent is added to this region. By providing the liquid reagent-receiving porous piece 1, when the liquid reagent is added, a fixed amount of the liquid can be supplied continuously for a relatively long time period to the porous piece 2 for retaining the dry labeled substance.

A sample-receiving porous piece or member 7 is disposed in a region around the detection site 4. It is necessary that at least one side or end of the sample-receiving porous piece 7 should be communicated with the test piece 3. The sample-receiving porous piece 7 and the test piece 3 must be disposed so that, when a sample is applied to the porous piece 7 in the first operation and flows into the test piece 3 through the porous piece 7, the detection site 4 is wetted immediately. However, the sample-receiving porous piece 7 should not cover the test piece 3 so as to disturb observation of complexes formed in the detection site 4.

The present invention does not employ a conventionally standard system wherein an analyte-containing sample mixed with a liquid reagent passes through a zone for retaining a labeled substance, and reacts in a detection site (as it were, a direct system by a one-step method). On the contrary, the system of the present invention involves previously immobilizing an analyte in the detection site, separately allowing only a liquid reagent to pass through the zone for retaining a labeled substance, and then allowing reaction to proceed (as it were, an indirect system by a two-step method). The present invention employs this system for the first time to thus enable accurate analysis without vague judgment. To ensure the operation of this system, the sample-receiving porous piece 7 is disposed independently from the test piece 3 (except the connection therebetween).

The system functions as follows. In the first operation, a given amount of a sample is applied to the sample-receiving porous piece 7, and passes through the piece 7 to reach the test piece of paper 3, thereby immediately wetting the detection site. This causes reaction of an analyte in the sample with a specific binding substance immobilized on the detection site, so that the analyte is immobilized on the detection site. Next, in the second operation, an appropriate liquid reagent is applied to the liquid reagent-receiving porous piece 1, and flows into the porous piece 2 for retaining a dry labeled substance. Thus, the labeled substance is dissolved by the liquid reagent and then migrates to the test paper 3. On the test paper 3, the liquid reagent migrates to the downstream toward the detection site, while washing away the liquid sample which has been applied in the first operation. When the liquid reaches the detection site, binding reaction of the labeled substance with the analyte immobilized on the detection site starts. Finally, within a short time period, the degree to which the label is accumulated in the detection site 4 can be measured.

Further, the system can be modified and applied to a competitive reaction. In this case, an analyte itself or its analog is used as the labeled substance contained in the porous piece 2.

Using an assay method based on the principles, a wide range of analytes can be measured by selecting each appropriate specific binding substance. Examples of analytes include proteins, immunoglobulins, hormones, steroids, drugs, viruses, bacteria, nucleic acids and the like.

Figure 2:
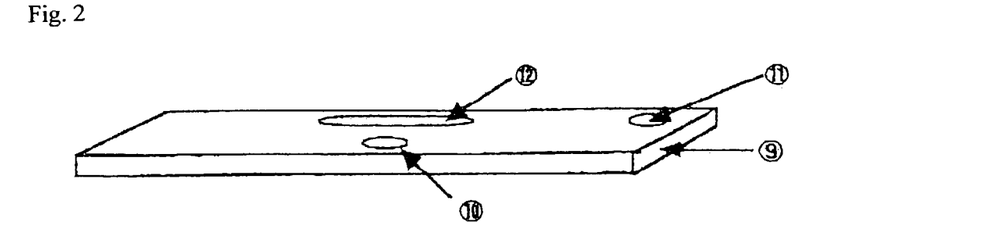
FIG. 2 shows an example of a finished analytical device according to the present invention.
Figure 3:
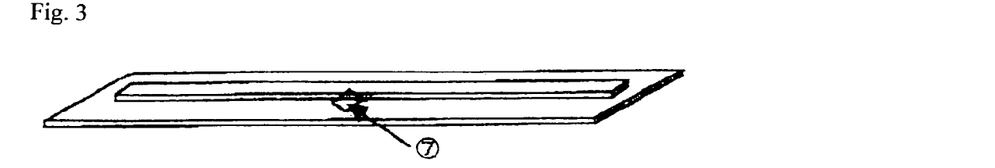
FIG. 3 shows the inside of the analytical device in FIG. 2.

FIG. 2 shows a finished analytical device using the above-mentioned porous test piece. FIG. 2 is a perspective view of the finished product, and FIG. 3 shows in detail the inside of the test piece of this device. As shown in FIG. 2, the device is card-shaped, and on its front, openings or holes or windows are provided: a circular sample hole 10 for applying a sample in the first operation; a circular liquid reagent-applying hole 11, to which a liquid reagent is applied in the second operation; and a rectangular observation hole 12 provided for observing test results. These holes are communicated with the porous pieces within the casing. The porous piece 7 communicated with the sample hole 10 is disposed so that it first receives a sample applied in the first operation, and allows the sample to migrate correctly to the detection site of the test piece which can be observed from the observation hole 12. The liquid reagent-applying hole 11 is communicated with the liquid sample-receiving porous member 1, and is disposed such that the liquid reagent is applied in the second operation, and then flows into the porous piece 2 containing a labeled substance.

The device according to the present invention comprises a test piece for analysis. Specifically, the device comprises a porous piece assembly and a sample-receiving porous piece 7, wherein the porous piece assembly comprises, from the upstream to the downstream: the liquid reagent-receiving porous piece 1; the labeled substance-retaining piece 2; the test piece 3 including a detection site 4 and, if necessary, a reference site 5; and as necessary, the absorbing porous piece 6. In the production of the porous piece assembly, the respective pieces are previously prepared independently. The pieces may be combined such that parts of the pieces are overlapping, or the pieces may be linked appropriately with porous members such that a liquid reagent can flow, or the pieces may be prepared as a unified piece. If necessary, to maintain the mechanical strength of the whole assembly or retain the pieces at respective correct positions, a porous support or lining sheet 8 may be disposed at the lower portion of the porous piece assembly and, if necessary, the sample-receiving porous piece.

Normally, an analytical test piece, i.e., the porous piece assembly and the sample-receiving porous piece 7, and optionally the lining sheet 8, are placed or accommodated in a hollow casing made of a moisture-impermeable material. The test piece-accommodating casing consists of the upper and lower portions, and the two portions may be formed as a single unit or formed separately. The test piece for analysis may be appropriately mounted in the lower portion. A concave portion, or conversely an apex portion, may be provided to facilitate mounting of the piece at a predetermined position. Further, in the upper portion, a liquid reagent-applying opening, a sample-applying opening, an observation window and the like are provided in the requisite positions.

Figure 4:
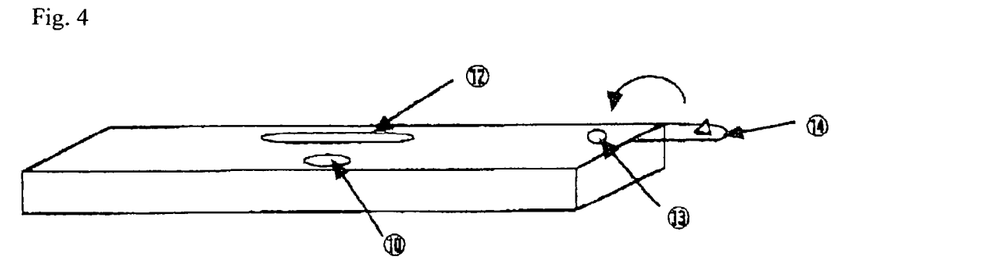
FIG. 4 shows another example of a finished analytical device according to the present invention.
Figure 5:
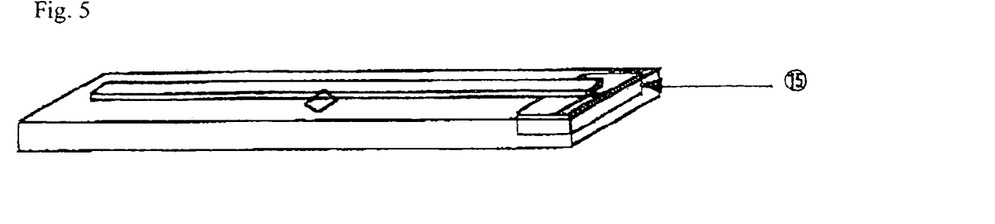
FIG. 5 shows the inside of the analytical device in FIG. 4.

An example of another form of a finished device is shown in FIGS. 4 and 5. FIG. 4 is a perspective view of a finished device which also employs a porous test piece but is different from the above device. FIG. 5 shows in detail the inside of the device. This device is different from the finished device as shown in FIGS. 2 and 3 in that this device contains in advance therein a liquid reagent to be supplied in the second operation. Specifically, the device is provided with a tank site 15 for retaining a liquid reagent under the liquid reagent-receiving porous site 1 of the test piece within the case. This tank is previously supplied directly with a liquid reagent, and is provided with an opening at its top portion which is sealed with, for example, an aluminum sheet, so as to prevent a liquid from leaking. The device is designed so as to be able to function by, after a sample is applied in the first operation, breaking an aluminum seal on the top of the tank site 15 in the second operation using a relatively sharp, pin-shaped projection through the hole or opening 13 shown in FIG. 4 to impregnate the liquid reagent-receiving porous site 1 at one end of the test piece with the liquid reagent within the tank. For example, the pin-shaped projection can be designed as shown in FIG. 4 (site 14). When the site 14 of the case, on which the projection is provided, is folded, the projection sticks into the opening 13, such that it punctures the aluminum seal located inside. Further, as another design, a bag or sachet, such as an aluminum bag, may be previously supplied with a liquid reagent, and placed in a built-in tank of the device, and the tank may be then fixed under the liquid reagent-receiving porous site 1. In the second operation, the pin-shaped projection provided at the site 14 of the case as shown in FIG. 4 sticks into the opening 13 when the site 14 is folded, so as to tear open the aluminum bag located inside.

The embodiment shown in FIGS. 4 and 5 is preferred since a user can start measurement by simply sticking the pin 14 into the window 13 immediately after application of a sample to the sample-applying hole. Therefore, a testing device can be provided for which the possibility of a mistake occurring in a series of operation procedure is low.

To manufacture the above-described device, for example, a plastic material is molded into two separate portions of the case. The porous members and the test piece are disposed in one portion of the case, which is then fixed with the other portion of the case, thus allowing easy assembly of the case.

With reference to a preferred example of the embodiment shown in FIGS. 4 and 5, a device for testing rubella antibody is described. The method described below is merely one example for explaining the present invention, and is not intended to limit the present invention. Further, various techniques of the prior art can be applied to the test piece used in the present invention, and the present invention is completed by disposing the test piece in a casing.

First, an example of a method for producing a test piece is described by referring to FIG. 1.

As a porous material for a test piece having a detection site and a reference site, for example, a membrane made of nitrocellulose can be used. In this example, SRHF membrane (Millipore) is used. Rubella virus antigen at a concentration of 0.5 mg/ml that has been purified by a sucrose density gradient method is coated in the form of a line by ink-jet printing technology on the detection site 4 at a rate of 1 µl/cm. Next, rabbit-derived anti-mouse IgG antibody dissolved in PBS at a concentration of 0.1 mg/ml is coated by ink-jet printing technology on the reference site 5 in the form of a line at a rate of 1 µl/ml. There exist various coating methods, such as a super small injector, a pen with adjustment pump, a direct printing and an ink-jet printing. For the purpose of the present invention, any of such techniques can be employed. A preferred method that is employed herein is a non-contact type printing technology having good quantitativity and causing no physical damage on the membrane. Coating may be performed on the membrane in various shapes, such as a dot, circle and cross. As the most efficient shape, coating is performed so as to draw a line which is vertical to the direction along which the labeled substance flows.

The coated membrane is dried thoroughly overnight in, for example a desiccator containing a drying agent, so as to aid firm binding of protein to the nitrocellulose membrane. The thoroughly dried membrane is allowed to be wetted with PBS (physiological saline) containing 1% BSA (bovine serum albumin) for 10 min, thereby blocking the region of the membrane to which protein has not yet been adsorbed. After blocking, the membrane is immersed in a 0.5% aqueous PVA (polyvinyl alcohol) solution for rinsing, and then thoroughly dried overnight. The washing process using this PVA is required to allow the membrane itself to retain its hydrophilicity when a sample or other liquid reagent is applied to the dry membrane. In addition to a polymer, such as PVA, a detergent, such as Tween 20 or Triton X-100, can be used.

As a porous member for retaining a labeled substance at the site 2 in FIG. 1, glass wool is employed. Colored latex, metal sol, dye and the like can be used as a label, and blue latex particles with a particle size of 0.13 µm (Bangs Laboratories, Inc.) are used herein. 1.5 mg of mouse-derived anti-human IgG monoclonal antibody is mixed with 100 µl of a 10% latex solution in a test tube, and then stirred overnight for binding. Furthermore, 1 ml of PBS solution containing 1% BSA is added to the mixture, and then stirred for another one hour, thereby blocking the unadsorbed latex region. After blocking, the mixture is centrifuged at 18,000 rpm for 20 min, thereby precipitating latex. After the supernatant are removed, 2% aqueous sucrose is added to re-solubilize the latex, thereby preparing the labeled substance. The resolubilized latex at 1% concentration is then coated on a porous material made of glass wool at a rate of 4 µl/cm. The coated porous material is thoroughly dried overnight.

When a test piece is assembled, an adhesive lining sheet 8 is used to retain and dispose each porous member. A membrane having the detection site and the reference site is first placed on the lining sheet, and then the labeled substance-coated porous member 2 is placed on the lining sheet so as to overlap by several mm on the upstream side of the membrane. Further, on the upstream side, the liquid reagent-receiving porous member 1 is placed such that it overlaps by several mm with the porous member containing the labeled substance. On the downstream side of the membrane, a liquid-absorbing porous member 6 for receiving the liquid reagent flowing thereinto is disposed so as to partially overlap with the membrane, thereby preparing a test piece. An important function in the preparation of a test piece is that the porous pieces or members are all communicated at least partially with each other when a liquid reagent is applied. The method using a lining sheet is one of the most convenient methods for preparing a test piece. A test piece can also be prepared by a method using no lining sheet. In this method, a casing itself has a structure for fixing each porous piece at a certain position.

Once the prepared test piece is placed in a case, the device of the present invention is finished. A finished device shown in FIG. 4 comprises a case which consists of an upper plastic part and a lower plastic part. The lower plastic part of the case contains a tank (site 15 in FIG. 5) for retaining a liquid reagent to be supplied in the second operation, and is provided with a frame for retaining a test piece and a frame for retaining a sample pad.

First, an appropriate amount of a liquid reagent (PBS containing 0.05% Tween 20) is added to the tank. The top of the tank is sealed with an aluminum sheet by heating, so as to prevent a liquid from leaking. It is required to add the liquid reagent in an amount necessary for transferring a labeled substance into a test piece and then to further downstream. Next, the test piece is fixed in the frame, so that the liquid reagent-receiving porous piece located on one end of the test piece is placed on the top of the tank sealed with the aluminum sheet. Subsequently, the sample pad can be fixed in the frame, so that one end of the pad overlaps by several mm with the test piece in the vicinity of the detection site. Thus, the upper part of the case is then combined with the lower part in which the test piece, sample pad and liquid reagent have all been disposed, so as to hold all the members including the test piece. That is, the test piece and sample pad are fixed, so that they are unable to move, and then the upper and lower parts of the case are adhered and fixed by, for example, heating, thereby completing the device of the present invention.

According to the present invention, precise measurement with improved sensitivity in which vague results are kept to a minimum can be implemented with a simple operation. The analytical device of the present invention is useful not only for medical practitioners, but also for individuals. Examples of test samples that can be tested by the analytical device include urine, whole blood and serum, and various other liquid samples. Thus, the use of the analytical device enables diagnosis of diseases, analysis of food and drink, inspection of food poisoning, analysis of environmental hormone, examination of chlamydia, and gene analysis of DNA and others.

What is claimed is:

1. An analytical device for assaying an analyte in a liquid sample, comprising:
    a test piece made of a porous material and having a first specific binding substance immobilized at a detection site stably even in the wet state, said test piece having an upper surface, a bottom surface and two side surfaces;
    a first porous member retaining a second labeled specific binding substance which is mobile in the wet state, the first porous member being in fluid communication with the test piece, wherein the second labeled specific binding substance is positioned apart from the detection site such that an analyte in a liquid sample introduced into the test piece reacts with the first specific binding substance before reacting with the second labeled specific binding substance;
    a second porous member to which a liquid reagent may be added, the second porous member being in fluid communication with the first porous member such that when the liquid reagent is applied to the second porous member the liquid reagent flows into the first porous member, solubilizes the second labeled specific binding substance, then flows into the detection site by capillary action; and
    a third porous member to which the liquid sample is added, the third porous member being adjacent to at least one of the sides of the test piece and in fluid communication with the test piece and the detection site such that when the liquid sample is applied to the third porous member, the liquid sample flows into the test piece by capillary action and wets the detection site;
    wherein the second porous member, the first porous member and the detection site are positioned in this order from upstream to downstream with regard to the flow of the liquid reagent; and
    wherein the third porous member is not in direct contact with the first porous member.

2. The device of claim 1, further comprising a reference site on the test piece, wherein the reference site is positioned downstream of the detection site, thereby confirming a normal flowing of the second labeled specific binding substance.

3. The device of claim 1, further comprising a fourth porous member for receiving the liquid sample and/or the liquid reagent overflowing the detection site, wherein the fourth porous member is in fluid communication with the downstream end of the test piece; and wherein the fourth porous member is not in direct contact with the third porous member.

4. The device of claim 2, further comprising a fourth porous member for receiving the liquid sample and/or the liquid reagent overflowing the detection and reference sites,
    wherein the fourth porous member is in fluid communication with the downstream end of the test piece; and
    wherein the fourth porous member is not in direct contact with the third porous member.

5. The device of claim 1, further comprising a casing composed of an upper part and a lower part, wherein:
    the casing is made of a moisture-impervious material for accommodating the test piece and the first, second and third porous members;
    the upper part of the casing includes an opening for applying the liquid sample to the third porous member, an opening for observing the detection site and an opening for applying the liquid reagent to the second porous member; and
    the third porous member is located under the opening for applying the liquid sample and the detection site is located under the opening for observing the detection site.

6. The device of claim 2, further comprising a casing composed of an upper part and a lower part, wherein:
    the casing is made of moisture-impervious material for accommodating the third porous member and the first, second and third porous members;
    the upper part of the casing includes an opening for applying the liquid sample to the test piece, an opening for observing the detection and reference sites and an opening for applying the liquid reagent to the second porous member; and
    the third porous member is located under the opening for applying the liquid sample and the detection and reference sites are located under the opening for observing the detection and reference sites.

7. The device of claim 3, further comprising a casing composed of an upper part and a lower part, wherein:
    the casing is made of a moisture-impervious material for accommodating the test piece and the first, second, third and fourth porous members;
    the upper part includes an opening for applying the liquid sample to the third porous member, an opening for observing the detection site and an opening for applying the liquid reagent to the second porous member; and
    the third porous member is located under the opening for applying the liquid sample and the detection site is located under the opening for observing the detection site.

8. The device of claim 4, further comprising a casing composed of a upper part and a lower part, wherein:
    the casing is made of moisture-impervious material for accommodating the test piece and the first, second, third and fourth porous members;
    the upper part includes an opening for applying the liquid sample to the third porous member, an opening for observing the detection and reference sites and an opening for applying the liquid reagent to the second porous member; and
    the third porous member is located under the opening for applying the liquid sample and the detection and reference sites are located under the opening for observing the detection and reference sites.

9. The device of any one of claims 5 to 8, wherein the lower part of the casing includes:
   (a) a container for containing an amount of the liquid reagent to be supplied to the second porous member, wherein the container is accommodated or provided within the casing; and
   (b) a means for puncturing the container when the liquid reagent is supplied to the second porous member.

10. The device of any one of claims 1 to 4, further comprising a barrier means made of a material which dissolves when contacting with the liquid sample or the liquid reagent, wherein the barrier means is positioned between the detection site and the first porous member, thereby stopping or retarding flowing of the liquid sample toward the first porous member.

11. The device of claim 10, wherein the material of the barrier means is sucrose or glycerol.

12. A method for assaying an analyte in a liquid sample by using the analytical device of any one of claims 1 to 8, comprising:
   applying a liquid sample suspected of containing an analyte to the test piece;
   allowing the analyte to react with and bind to the immobilized first specific binding substance;
   supplying a liquid reagent to the second porous member; and
   detecting the second labeled specific binding substance immobilized in the detection site.

13. A method for assaying an analyte in a liquid sample by using the analytical device of any one of claims 1 to 8, comprising:
   applying a liquid sample suspected of containing an analyte to the third porous member;
   allowing the analyte to react with and bind to the immobilized first specific binding substance;
   supplying a liquid reagent to the second porous member; and
   detecting the second labeled specific binding substance immobilized in the detection site.

14. A method for assaying an analyte in a liquid sample by using the analytical device of claim 9, comprising:
   applying a liquid sample suspected of containing an analyte to the third porous member; allowing the analyte to react with and bind to the immobilize immobilized first specific binding substance;
   supplying a liquid reagent to the second porous member; and
   detecting the second labeled specific binding substance immobilized in the detection site.

15. A method for assaying an analyte in a liquid sample by using the analytical device of claim 10, comprising:
   applying a liquid sample suspected of containing an analyte to the third porous member;
   allowing the analyte to react with and bind to the immobilize immobilized first specific binding substance;
   supplying a liquid reagent to the second porous member; and
   detecting the second labeled specific binding substance immobilized in the detection site.

16. A method for assaying an analyte in a liquid sample by using the analytical device of claim 11, comprising:
   applying a liquid sample suspected of containing an analyte to the third porous member;
   allowing the analyte to react with and bind to the immobilize immobilized first specific binding substance;
   supplying a liquid reagent to the second porous member; and
   detecting the second labeled specific binding substance immobilized in the detection site.

17. A method for assaying an analyte in a liquid sample by using the analytical device of claim 12, comprising:
   applying a liquid sample suspected of containing an analyte to the third porous member;
   allowing the analyte to react with and bind to the immobilize immobilized first specific binding substance;
   supplying a liquid reagent to the second porous member; and
   detecting the second labeled specific binding substance immobilized in the detection site.

18. The analytical device according to claim 1 wherein:
   the first porous member is in direct fluid communication with the test piece;
   the second porous member is in direct fluid communication with the first porous member; and
   the third porous member is in direct fluid communication with the test piece.

19. An analytical device according to claim 1 wherein:
   the first porous member is in indirect fluid communication with the test piece;
   the second porous member is in indirect fluid communication with the first porous member; and
   the third porous member is in indirect fluid communication with the test piece.

* * * * *

UNITED STATES PATENT AND TRADEMARK OFFICE
CERTIFICATE OF CORRECTION

PATENT NO. : 7,270,995 B2  Page 1 of 1
APPLICATION NO. : 10/296383
DATED : September 18, 2007
INVENTOR(S) : Hirohisa Matsushita, Hidenori Kawai and Takashi Kitoh It is certified that error appears in the above-identified patent and that said Letters Patent is hereby corrected as shown below:

Title Page;

1. In section [73] Assignee:

Change "Nichirei Biosciences" to --Nichirei Biosciences Inc.--

Signed and Sealed this

Seventh Day of July, 2009

JOHN DOLL
*Acting Director of the United States Patent and Trademark Office*